(12) United States Patent
Mayer et al.

(10) Patent No.: US 10,154,858 B2
(45) Date of Patent: Dec. 18, 2018

(54) DEVICE FOR PREPARING AN OPENING IN TISSUE FOR IMPLANTATION OF AN IMPLANT

(71) Applicant: SpineWelding AG, Schlieren (CH)

(72) Inventors: Jörg Mayer, Niederlenz (CH); Andreas Wenger, Muri b. Bern (CH); Philipp Seiler, Niederdorf (CH); Stephanie Mehl, Zug (CH); Milica Berra, Schlieren (CH)

(73) Assignee: SPINEWELDING AG, Schlieren (CH)

( * ) Notice: Subject to any disclaimer, the term of this patent is extended or adjusted under 35 U.S.C. 154(b) by 0 days.

(21) Appl. No.: 15/346,982

(22) Filed: Nov. 9, 2016

(65) Prior Publication Data

US 2017/0049478 A1 Feb. 23, 2017

Related U.S. Application Data

(62) Division of application No. 14/160,703, filed on Jan. 22, 2014, now Pat. No. 9,510,861, which is a division
(Continued)

(51) Int. Cl.
| | |
|---|---|
| *A61B 17/68* | (2006.01) |
| *A61B 17/88* | (2006.01) |
| *A61B 17/00* | (2006.01) |
| *A61F 2/30* | (2006.01) |
| *A61F 2/28* | (2006.01) |

(52) U.S. Cl.
CPC ........ *A61B 17/686* (2013.01); *A61B 17/8822* (2013.01); *A61B 2017/00004* (2013.01); *A61B 2017/00955* (2013.01); *A61F 2/28* (2013.01); *A61F 2002/2839* (2013.01); *A61F 2002/30065* (2013.01); *A61F 2210/0071* (2013.01)

(58) Field of Classification Search
CPC ......................................... A61B 17/68–17/688
See application file for complete search history.

(56) References Cited

U.S. PATENT DOCUMENTS

| | | | |
|---|---|---|---|
| 2002/0124402 A1 | 9/2002 | Berthelet et al. | |
| 2004/0030341 A1* | 2/2004 | Aeschlimann ... | A61B 17/00491 606/232 |

(Continued)

FOREIGN PATENT DOCUMENTS

| | | |
|---|---|---|
| EP | 2596764 | 5/2013 |
| WO | 02/069817 | 9/2002 |

(Continued)

*Primary Examiner* — Zade Coley
(74) *Attorney, Agent, or Firm* — Rankin, Hill & Clark LLP

(57) ABSTRACT

A device for preparing an opening in tissue for implantation of an implant. The device includes a tool adapted to be coupled to an energy source, an augmentation element of a thermoplastic material, and a counter element. A tool contact surface and a first augmentation element contact surface together form a first interface, and a second augmentation element contact surface and a counter element contact surface together form a second interface. The device is configured to be being inserted into an opening in the tissue and configured for the augmentation element to be compressed between the tool and the counter element while at the same time energy is coupled into the tool.

10 Claims, 2 Drawing Sheets

Related U.S. Application Data of application No. 13/125,072, filed as application No. PCT/CH2009/000339 on Oct. 22, 2009, now Pat. No. 8,663,297.

(60) Provisional application No. 61/107,757, filed on Oct. 23, 2008.

(56) References Cited

U.S. PATENT DOCUMENTS

| | | | |
|---|---|---|---|
| 2007/0265704 A1* | 11/2007 | Mayer | A61B 17/0469 623/11.11 |
| 2008/0109080 A1* | 5/2008 | Aeschlimann | A61B 17/0401 623/16.11 |
| 2008/0199249 A1 | 8/2008 | Clinch et al. | |
| 2009/0131947 A1 | 5/2009 | Aeschlimann et al. | |
| 2011/0077696 A1 | 3/2011 | Schlottig et al. | |
| 2013/0144335 A1 | 6/2013 | Sandow | |

FOREIGN PATENT DOCUMENTS

| | | | |
|---|---|---|---|
| WO | 2004/017857 | 3/2004 | |
| WO | 2005/079696 | 9/2005 | |
| WO | 2008/034276 | 3/2008 | |
| WO | 2008/034277 | 3/2008 | |
| WO | WO 2008034278 A1 * | 3/2008 | B29C 65/645 |
| WO | 2008/095327 | 8/2008 | |

* cited by examiner

DEVICE FOR PREPARING AN OPENING IN TISSUE FOR IMPLANTATION OF AN IMPLANT

CROSS-REFERENCE TO RELATED APPLICATION

This application is a division of U.S. application Ser. No. 14/160,703 filed Jan. 22, 2014, which is a division of U.S. application Ser. No. 13/125,072, filed Jun. 27, 2011, which is a U.S. National Stage Application of PCT/CH2009/000339, filed Oct. 22, 2009, and claims priority to U.S. Provisional Application No. 61/107,757, filed Oct. 23, 2008.

BACKGROUND OF THE INVENTION

Field of Invention

The invention is in the field of anchoring objects in hard tissue and/or hard tissue replacement material, such as bone. Especially, it is suited for anchoring objects in weak or brittle hard tissue, such as osteoporotic bone.

Description of Related Art

If screws are anchored in live bone tissue, often the problem of insufficient bone stability or insufficient stability of the anchoring in the bone arises. Especially, in trabecular bone tissue, any load acting on the screw is passed over to only few trabeculae, with adverse consequences both for the load bearing capability of the screw-bone connection and for its long-time stability. This is especially severe in osteoporotic or otherwise weakened bone tissue.

BRIEF SUMMARY OF THE INVENTION

It is an object of the present invention to provide methods and devices for anchoring implants overcoming disadvantages of prior art implant anchoring methods.

According to a first aspect of the invention, a method of anchoring an implant in hard tissue and/or hard tissue replacement material is provided, the method comprising the steps of providing an initial opening in the hard tissue and/or hard tissue replacement material, of providing a thermoplastic augmentation element, a tool and a counter element, of compressing the augmentation element between the tool and the counter element while energy is coupled into the tool and/or the augmentation element and while a periphery of a liquefaction interface of the oscillation tool and the augmentation element and/or of a liquefaction interface of the augmentation element and the counter element is in the opening, thereby liquefying material of the augmentation element at the liquefaction interface(s) to yield liquefied material, causing portions of the liquefied material to penetrate into structures of the hard tissue and/or hard tissue replacement material or connected thereto, allowing the liquefied material to harden and to thereby become augmentation material, removing the oscillation tool and the counter element, and anchoring the implant in the opening comprising at least some of the augmentation material.

The tool may be an oscillation tool, and the step of coupling energy into the tool and/or the augmentation element may then comprise coupling mechanical oscillations into the oscillation tool. The material is caused to liquefy at the interface due to external and/or internal friction.

As an alternative, the tool may be caused to rotate, whereby the energy coupled into the system is rotational mechanical energy, the material being caused to liquefy at the interface due to friction.

As yet another alternative, electromagnetic radiation may be coupled, for example, by the tool into the augmentation element (which then is essentially transparent for the electromagnetic radiation at the used wavelength), and may be absorbed at the interface so that the heat arising therefrom causes the liquefaction.

As an even further alternative, the tool may be a heater provided with a heater, whereby the energy coupled into the system is heat.

The structures may be structures of a circumferential wall of the opening if the opening is a bore-like structure. For example, if the hard tissue and/or hard tissue replacement material comprises cancellous bone, the structures may include the structures of trabeculae with spaces between them. If the hard tissue and/or hard tissue replacement material comprises cortical bone, the structures may include structures of the cortical bone. If the if the hard tissue and/or hard tissue replacement material is a porous bone replacement material—such as a metallic foam or a hydraulic cement or an autograft or allograft bone, the structures comprise pores or other structures of such bone replacement material. In this, the opening may also be an opening with a circumferential wall that does not surround the interface without any interruption, but that for example is a gap of a joint.

Alternatively, the structures may be structures of a device connected to the hard tissue and/or hard tissue replacement material. For example, pedicle screws for spine stabilization devices have become known, which pedicle screws comprise a radially expandable segment or element. The expandable segment or element expands within the cancellous bone during the surgical implantation and creates a channel with a porous wall that allows interdigitation for example by cement. The approach described herein allows filling of the channel and the porous wall of the element/segment by thermoplastic material from within the device.

The interface between the tool and the augmentation element (and/or, as the case may be, between tool and counter element) where liquefying takes place defines a liquefaction interface (or, if liquefaction takes place at the two interfaces, define two liquefaction interfaces). Usually and preferably, the interface between the tool and the augmentation element is the liquefaction interface.

In case the energy coupled into the system is oscillation energy, the system may as an alternative be designed so that the liquefaction interface is the interface between the counter element and the augmentation element (solely or in addition to the interface between the tool and the augmentation element). To this end, the augmentation element comprises special shape—for example it may be substantially thinner at the interface to the counter element, so that the oscillations may be transmitted through the augmentation element towards the counter element, and also the interface between the counter element and the augmentation element may be the liquefaction interface.

Also in case the energy coupled into the system is rotational energy, it is possible to cause the liquefaction interface to be the interface between the counter element and the augmentation element, for example by coupling the augmentation element to the rotation tool so that the rotational mechanical movement is coupled into the augmentation element as well and the friction arises at the interface between the counter element and the augmentation element.

Finally, if the energy is radiation energy or heat, the interface(s) at which liquefaction takes place may be chosen in accordance with the particular needs.

In the following text, the expression "augmentation process" refers to the sub-sequence of the following steps:

placing the augmentation element, the tool and the counter element so that a periphery of the liquefaction interface(s) is/are adjacent the circumferential wall, compressing the augmentation element between the tool and the counter element energy is coupled into the oscillation tool and while a periphery of the liquefaction interface(s) is in the opening, thereby liquefying material of the augmentation element to yield liquefied material, causing portions of the liquefied material to penetrate into structures of the hard tissue and/or hard tissue replacement material or device connected thereto, allowing the liquefied material to harden and to thereby become augmentation material, and removing the tool and the counter element.

It is an aspect of the invention to provide the concept of an augmentation process of hard tissue with the aim of anchoring an other object by means of mechanical oscillations, for example ultrasonic vibrations.

The steps of allowing the liquefied material to harden and of removing the tool and the counter element may be carried out one after the other in arbitrary sequence, or may be carried out simultaneously. Often, the augmentation material is caused to augment an extended part of the circumferential surface, i.e. has a substantial axial extension. Then, the augmentation process includes moving the liquefaction interface(s) or at least one liquefaction interface in an axial direction while the energy impinges (i.e. for example while the oscillations act). In such a situation, the hardening in one region may have taken place while in another region, at an axial distance from the one region, the liquefaction may still take place.

The augmentation process can be repeated several times, so that over the length of the opening several desired spots are augmented. As an example, for a pedicle screw, an augmentation may be carried out distally within the vertebral body, medially in the region of the pedicle, and maybe even proximally for the enforcement of the proximal lamina.

From the liquefaction interface, during the liquefaction step, the liquefied material flows usually radially outward into the structures of the hard tissue and/or hard tissue replacement material (or, as the case may be, of the device connected thereto). Thus, a periphery of the liquefaction interface forms a part of the peripheral interface of the tool—augmentation-element—counter-element assembly. The structures of the hard tissue and/or hard tissue replacement material may be a porous structure made up of spaces between trabeculae or similar. They may also be artificially added or naturally occurring roughnesses or the like. Almost any structure that deviates from an even surface is suitable, however, structures with 'undercut' like features are preferable.

A first special class of hard tissue/hard tissue replacement material suitable to be augmented by the method according to the invention is trabecular bone, for example osteopenic or osteoporotic bone. A second special class of hard tissue/hard tissue replacement material where the invention is especially useful is spongy bone substitute material such as autograft or allograft bone tissue (including cadaver bone material), trabecular metal (especially titanium foam or tantalum foam), or hydraulic cement such as used for vertebroplasty. The approach according to the invention thus allows to use, as hard tissue replacement material, spongy, porous material that is highly suitable for ingrowth of real bone material, and to nevertheless soundly anchor the implant in it.

Even though the opening in the hard tissue and/or hard tissue replacement material may be a blind hole, a gap (of a joint or the like) or a through opening, the removal of both, the tool and the counter element in many embodiments has to take place to one and the same side, namely to the proximal side. This implies that in these embodiments the augmentation material will leave a final opening through which the distal portion of the tool or the counter element is pulled during the augmentation process. The cross sectional area of the final opening will, thus, at least be equal to the cross sectional area of the most distal portion of the oscillation tool or the counter element, respectively. This distal portion, however, is the portion that serves for compressing the augmentation element during the liquefaction of the thermoplastic material. Thus, during the augmentation process, the whole augmentation element (or at least a whole axial section of it) has to be completely displaced outwardly from its initial position. If the augmentation element is tube shaped or has the shape of a plurality of connected or unconnected tube sectors, an inner diameter of the final opening will thus be greater than an average diameter of the augmentation element before the augmentation process. In other words, according to a further aspect, the augmentation material during the augmentation process is displaced from an initial, inner position to a final, outer position, by at least a radial distance that corresponds to half a wall thickness of the tube wall of the augmentation element.

According to a preferable version, an inner diameter of the augmentation material remaining anchored in the hard tissue and/or hard tissue replacement material after the augmentation process may even be larger than an outer diameter of the augmentation element prior to the augmentation process. Thus the tool—or potentially the counter element—is moved, during the augmentation process through the—entire—space where the augmentation element was placed at the onset of the liquefaction step.

Also, preferably, during liquefaction an entire cross section of the augmentation element is liquefied. The liquefaction interface to this purpose covers, in a projection along a movement axis that may also be an opening axis, an entire cross section of the augmentation element. The liquefaction step therefore includes continuously melting away, at the liquefaction interface an entire cross section of the augmentation element and displacing it outwardly into and onto the structures of the opening, while the liquefaction interface moves with respect to the counter element (and/or to the tool) and to the body of the remaining augmentation element to continuously 'eat away' the remaining augmentation element. The process may, according to a preferable variant, be continued until the tool contact surface and the counter element contact surface contact each other, so that the augmentation element is fully displaced ('used up'). However, it is also possible to stop the process and to remove remaining augmentation element portions together with and between the tool and the counter element.

In many embodiments where the liquefaction interface is the interface between the tool and the augmentation element, not only the liquefaction interface is subject to an axial movement, but also the interface between the augmentation element and the counter element. Then, an overall length of the augmentation material is shorter than an initial length of the augmentation element.

There are two basic configurations of the method and device according to the invention. In a first, preferred configuration, the tool contact surface is at a distal end of the augmentation element, and the force for compressing the augmentation element is coupled into the tool as a tensile force—the tool is pulled. To that effect, the tool may comprise a shaft portion and a distal broadening, a rearward (i.e. towards the proximal side) facing surface forming the tool contact surface. The counter element then is a "pusher" that may be moved forward (towards the distal side) during the liquefaction step, or that may be held still, depending on how much augmentation material per axial length unit is to be disposed. The counter element may, for example, be of a rigid material with a tube shaped end forming the counter element contact surface. It is in any case preferred if the counter element can optionally be pushed forward and into the opening during the process. If, however, the counter element is not to be moved forward, it may also have the shape of a plate to be held against the hard tissue and/or hard tissue replacement material surface, or similar.

This "retro" configuration features the advantage of providing maximum flexibility while keeping the contact surfaces between the tool and the sensitive tissue surface at a minimum.

In a second, "forward" configuration, the tool contact surface is at a proximal end of the augmentation element, and the force for compressing the augmentation element is coupled into the tool as a pressing force—the tool is pushed. Then, it is the counter element that reaches to the distal side and may comprise a shaft portion and a distal broadening with a rearward facing surface forming the counter element contact surface.

In the "retro" configuration, the tool may, in addition to the augmentation process, serve a different purpose. During insertion, in a first, forward movement the tool may also be used for creating or expanding the opening in the hard tissue/hard tissue replacement material by means of a cutter and/or chisel like function by having, on a distal side, appropriate shapes. Such cutter and/or chisel like functions are as such known from ultrasound processing/machining of bone and tooth material. By this measure, a process step can be saved, and also holes can be created and augmented that do not have a circular cross section.

In any configuration, the augmentation element may comprise an axially through-going, for example central, opening for the tool (for the retro configuration) or for the counter element (for the forward configuration). The axis of the central opening which is preferably parallel to the movement axis and to the opening axis. The augmentation element may for example be essentially tube shaped or comprise one or a plurality of sections (sectors) covering different angle ranges (the sectors, by their arrangement defining the central opening). It may, however, also be configured differently and, for example, comprise helical structures or the like.

The implant may be a fastening device for fastening other objects to the tissue or for fastening tissue parts to each other. The implant as an alternative may also serve as any kind of prosthesis.

For implantation of the implant in the augmented opening, anchoring structures of the implant are brought in intimate contact with the thermoplastic augmentation material. The intimate contact may be such as to cause a mechanical anchoring, such as a positive-fit anchoring, and/or such as to cause an anchoring by bonding.

The implant to be anchored in the opening may therefore, according to a first embodiment of the invention comprise fastening and/or retention structures for a mechanical connection (mechanical anchoring), for example by a positive fit connection. Examples of such fastening and/or retention structures are a thread, a barbed structure, rivet-kind structures etc. These structures are preferably such as to engage into the augmented hard tissue and/or hard tissue replacement material, i.e. with reference to a hole axis of the initial hole, they reach further out than the hole radius. As a second embodiment, in addition or as an alternative, the implant to be implanted may comprise surface material portions that may be bonded (positively bonded, substance-to-substance bonded; adhesive bonded) to the augmentation material, for example by welding.

If formed according to the first embodiment, the implant may comprise a threaded section and act as screw. The thread of the screw then engages into the hard tissue and/or hard tissue replacement material augmented by the augmentation material. The screw diameter in this situation is chosen so that an outer diameter of the threaded section is greater than a diameter of the initial opening.

Depending on the size of the threaded section and on parameters of its thread—such as the thread pitch and the thread height, the augmented hard tissue and/or hard tissue replacement material may produce a substantial resistance against introduction of the threaded section. If this is the case, in the augmentation process according to the invention, the tool (and/or potentially the counter element) may comprise structures for conditioning the augmentation material to ease introduction of a thread. For example, the tool may comprise radially protruding blades confining the flow of the liquefied thermoplastic material to certain azimuthal angles. Thereby the augmentation material obtains a slitted structure that offers less resistance to radial expansion by an element introduced into the opening. As an alternative, the tool may comprise a rotatably mounted thread cutting section to directly cut a thread during the augmentation process.

If formed according to the second embodiment, the implant may be formed as for example described in WO 02/069 817, WO 2004/017 857, WO 2005/079 696, WO 2008/034 277, or U.S. provisional patent application 60/983, 791, the teaching of all of these references being incorporated herein by reference. All these references teach to liquefy thermoplastic material by mechanical oscillations and to cause liquefied thermoplastic material to penetrate into porous structures of the tissue they are to be anchored in. When used in combination with the approach according to the invention, however, the thermoplastic material of the implant will at least partially be welded together with the augmentation material, instead of or in addition to forming a positive-fit connection. If, according to the second embodiment, a bond is formed between the augmentation material and material of the implant, welding by means of applying mechanical oscillations to the implant is preferred, because then the thermoplastic material is melted only locally at surface portions, for example at the places of energy directors. By this measure, the overall heat impact is substantially lower, and the use of thermoplastic materials with melting temperatures substantially above 37° C. is readily possible. Nevertheless, the invention does not exclude the welding by other means, such as by thermal heating, especially if the implant is very small, at places where the heat impact does not produce extensive damages and/or if the melting temperature of the thermoplastic augmentation materials and/or the thermoplastic implant material is not far above 37° C.

The thermoplastic material of the augmentation element may be homogeneous or made up of different components (such as of an inner and an outer layer of different hardness). The thermoplastic material may be non-resorbable or may be at least partly resorbable. If the primary stability provided by the augmentation material is to be retained, the thermoplastic material is not resorbable or only partly resorbable.

Suitable Resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene. An overview table of polymers and applications is listed in Wintermantel, page 150; specific examples can be found in Wintermantel page 161 ff. (P E, Hostalen Gur 812, Höchst A G), pages 164 ff. (PET) 169ff. (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

Examples of suited thermoplastic material include polylactides such as any one of the products LR708 (amorphous Poly-L-DL lactide 70/30), L209 or L210S by Böhringer Ingelheim or polycarbonates.

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

Fillers used may include degradable, osseostimulative fillers to be used in degradable polymers, including: β-Tricalcium phosphate (TCP), Hydroxyapatite (HA, <90% cristallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), JA Juhasz et al. Biomaterials, 2004 March; 25(6):949-55. Particulate filler types include: coarse type: 5-20 μm (contents, preferentially 10-25% by volume), sub-micron (nanofillers as from precipitation, preferentially plate like aspect ratio>10, 10-50 nm, contents 0.5 to 5% by volume).

More generally liquefaction is achieved by using materials with thermoplastic properties having a melting temperature of up to about 350° C. In embodiments in which the energy is a mechanical oscillation energy and the tool is an oscillation tool, if the liquefaction interface or one of the liquefaction interfaces is between the augmentation element and the counter element, the modulus of elasticity should be at least 0.5 GPa so that the thermoplastic material transmits the mechanical oscillation with such little damping that inner liquefaction and thus destabilization of the augmentation element does not occur, i.e. liquefaction occurs only where the liquefiable material is at the liquefaction interface. If only the interface to the oscillation tool serves as the liquefaction interface, the material may in principle also have a lower modulus of elasticity. However, due to the load bearing function the material has, also in this situation a modulus of elasticity should of at least 0.5 GPa is preferred.

The mechanical oscillations applied have of a frequency preferably in the rage of between 2 and 200 kHz (preferably ultrasonic vibration).

BRIEF DESCRIPTION OF THE DRAWINGS

In the following, embodiments of the invention are described in connection with the following figures, wherein same reference numerals refer to same or equivalent elements. Therein.

DESCRIPTION OF THE PREFERRED EMBODIMENTS

Figure 1:
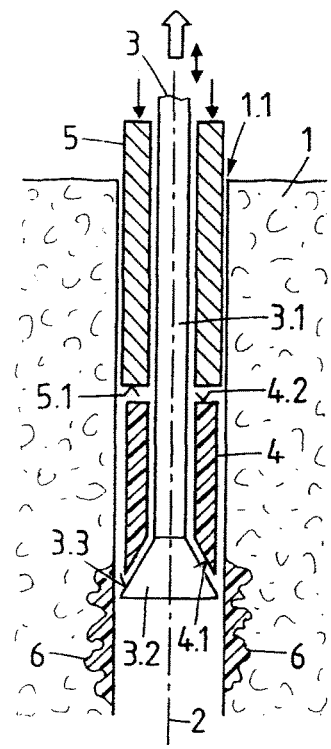
FIG. 1 depicts a first embodiment of a device and a method according to the invention.

The device shown in FIG. 1 is illustrated partly inserted in an opening in bone tissue 1. The opening preferably is translation symmetrical with respect to translations parallel to an axis 2, but may have any cross section perpendicular to that axis. For many embodiments, though, the opening has the shape of a circular cylinder, i.e. the cross section is circular. The opening 1.1 may have been added to the bone tissue by a conventional method, such as by drilling.

The device parts, as far as to be inserted in the opening 1.1, are rotational symmetric if the opening is circular in cross section. They comprise an oscillation tool 3, an augmentation element 4, and a counter element 5. The augmentation element 4 is formed as a tube of a suitable thermoplastic material.

The oscillation tool 3 may be metallic and comprises a tool shaft 3.1 reaching through the augmentation element 4 from a proximal side to a distal side. At the proximal side, the oscillation tool comprises means (not illustrated) for the tool to be coupled to an oscillation generator, such as an ultrasonic device. The means are such that a tensile force may be coupled into the oscillation tool. At the distal side, the tool comprises a distal broadening 3.2 joined to the shaft 3.1. The distal broadening has the shape of a wedge tapering from the distal to the proximal side where it is attached to the shaft.

The backward-facing surface 3.3 (i.e. the tapering surface facing towards the proximal side) of the distal broadening 3.2 serves as an oscillation tool contact surface and oscillation tool coupling-out surface when in contact with a distal first contact surface 4.1 of the augmentation element. Together, the oscillation tool contact surface 3.3 and the augmentation element first contact surface 4.1 form the liquefaction interface.

The proximal end surface of the augmentation element forms the second augmentation element contact surface 4.2 against which the counter element contact surface 5.1 can be pressed during augmentation.

The counter element 5 is tube shaped with a wall thickness preferably equal to or greater than the wall shape of the augmentation element. The counter element may be metallic or of a suitable plastic or ceramic material.

During the augmentation process, mechanical oscillations and a tensile force are coupled into the oscillation tool 3, while the counter element is held against the tensile force by a pushing force. Due to the effect of the mechanical oscillations, the thermoplastic material melts at the liquefaction interface. While liquefaction progressively continues at the liquefaction interface, the oscillation tool is pulled towards the proximal side, and/or the counter element is pushed towards the distal side, so that the length of the remaining, not yet molten augmentation element portion gradually decreases. Due to the wedge shape of the distal broadening and due to the lack of other space to go to, the melted augmentation material is pushed sideways into the structures such as openings, and/or pores of the bone material around the circumferential wall of the opening 1.1. Thereby the augmentation material forms an augmentation zone 6 in the bone tissue around the opening where the bone material is interpenetrated by the again hardened thermoplastic augmentation material. The cross section of the remaining final opening may, depending on the cross section of the distal broadening of the oscillation tool, be approximately equal to the cross section of the initial opening, or slightly less than that. The length (measured along the axis 2) of the augmentation zone 6 may be approximately equal as the initial length of the augmentation element 4, or it may be less than that, depending on whether the counter element 5 is held still during the augmentation process (then the length will be equal) or whether the counter element is pushed forward during the augmentation process (then the length will be smaller, and the material in the augmentation zone 6 per length unit will be greater than the initial material per length unit of the augmentation element.

Figure 2:
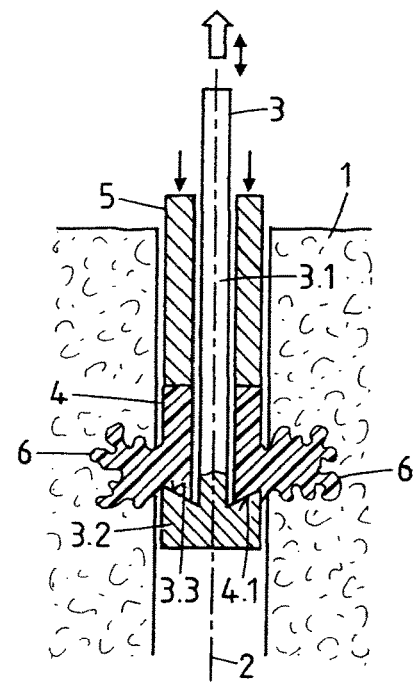
FIG. 2 shows a second embodiment of a device and a method according to the invention.

FIG. 2 depicts a variant of the device and method of FIG. 1. As a first difference, the distal broadening on the rearward side comprises a face (forming the oscillation tool contact surface) that tapers inward, i.e. that defines a concave structure. The inclination with respect to an axis normal plane may for example be between 10° and 60°, especially around 45°. Such inward tapering has been found to be especially advantageous in terms of melting properties: it prevents the augmentation element from merely being softened, pushed outward and put over the distal broadening without being properly liquefied. Rather, it centers the augmentation element with respect to the oscillation tool and ensures thorough liquefaction at the liquefaction interface.

The device as depicted in FIG. 2 can be used like the one of FIG. 1 and be pulled through the opening 1.1 to leave an axially extended augmentation zone of desired length, as discussed above.

The configuration depicted difference in FIG. 2, shows, as second difference to FIG. 1, the concept of reduced length of the augmentation zone 6 being taken to an extreme: the oscillation tool is held still during the augmentation process, so that the entire axial movement in the augmentation process stems from the forward movement of the counter element 5. This results in a ring-shaped (instead of tube-shaped) augmentation zone 6.

A set-up as the one illustrated in FIG. 1 or 2 may also be used if the energy is coupled into the system by way of rotation of the tool 3. In this, preferably there is a rotational coupling between the augmentation element 4 and the counter element 5. For example, the augmentation element may stick to the surface of the counter element, and/or the augmentation element and the counter element may comprise interdigitating structures. Friction then causes the augmentation element to melt at the interface between the augmentation element 4 and the tool 3. If, in contrast, the augmentation element is rotationally coupled to the tool and decoupled from the counter element, the liquefaction will take place at the interface between the augmentation element and the counter element.

Figure 3:
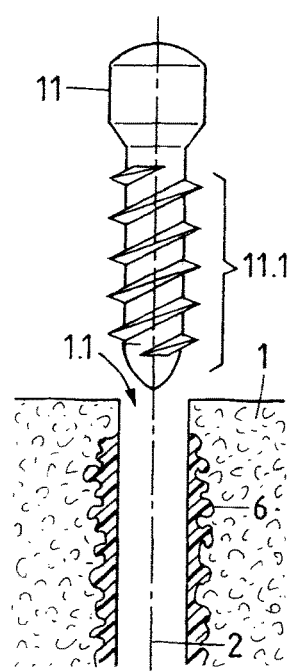
FIG. 3 schematically illustrates implantation of an implant in an opening in bone tissue augmented by a method according to the invention.

FIG. 3 illustrates the anchoring of an implant 11 in the opening 1.1 augmented by the augmentation zone 6. The major diameter of the threaded section 11.1 of the screw is greater than the diameter of the initial opening 1.1 so that the thread engages into the bone material in the region of the augmentation zone. The augmentation material of the augmentation zone helps to distribute the mechanical load in the bone material and prevents single trabeculae from being loaded too heavily.

Figure 4:
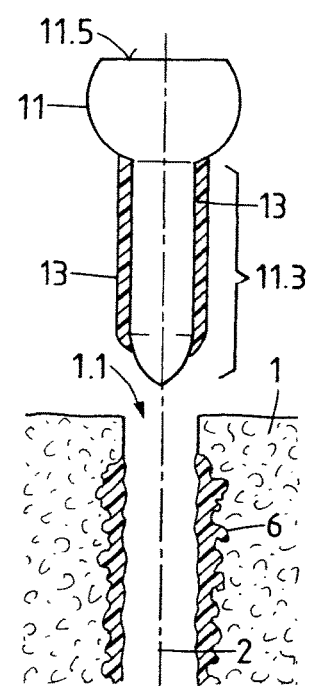
FIG. 4 illustrates implantation of a different implant.

FIG. 4 depicts an alternative embodiment that, in contrast to the embodiment of FIG. 3, is also suitable for openings 1.1 with non-circular cross sections. The implant 11 comprises a surface or surface regions of thermoplastic material 13. The implant may, for example, consist entirely of the thermoplastic material or may be, as depicted, a hybrid implant with a, for example, metallic or ceramic core and thermoplastic surface portions. If the implant is a hybrid implant, the thermoplastic surface portions may entirely cover a circumferential surface of an anchoring portion 11.3 to be anchored in the bone tissue or only portions thereof, as for example taught in embodiments of WO2004/017857, the content of which is incorporated herein by reference. The implant 11 further comprises a coupling-in surface 11.5 suitable for a sonotrode to engage to couple mechanical oscillations into the implant. For implantation, the implant is pushed into the opening at least to a certain extent, and then mechanical oscillations are coupled into it, while the implant may optionally be further pushed into the opening. Due to the effect of the mechanical oscillations and the frictional forces created at the periphery of the anchoring portion 11.3, the thermoplastic material 13 starts melting and welds to the augmentation material of the augmentation zone. Optionally, in addition portions 13 of the thermoplastic material may be pushed into structures of the bone material so that an additional anchoring of the kind taught in WO02/069817, also incorporated herein by reference, is achieved.

The thermoplastic material 13 of the implant 11 of FIG. 4 does not need to surround the implant shaft. Also, the cross section of the implant need not be circular, also in cases where the opening is circular (and the implant then may comprise self-reaming structures). For example, if the cross section is a double-T-shape the thermoplastic material may in an embodiment cover the bridge portion of the double T only.

Figure 5:
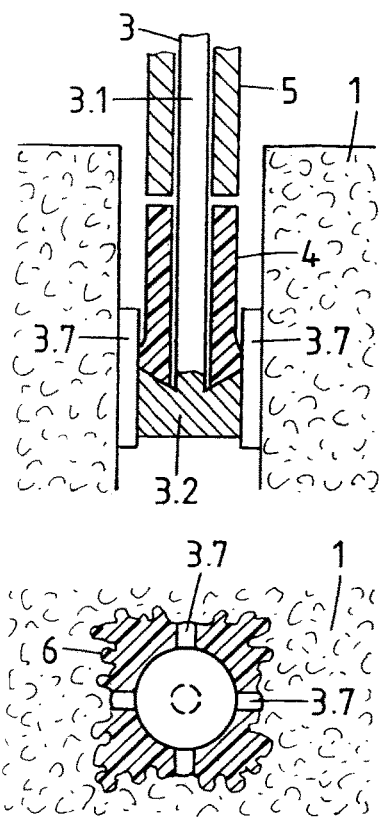
FIG. 5 depicts a further embodiment of a device and a method according to the invention.
Figure 6:
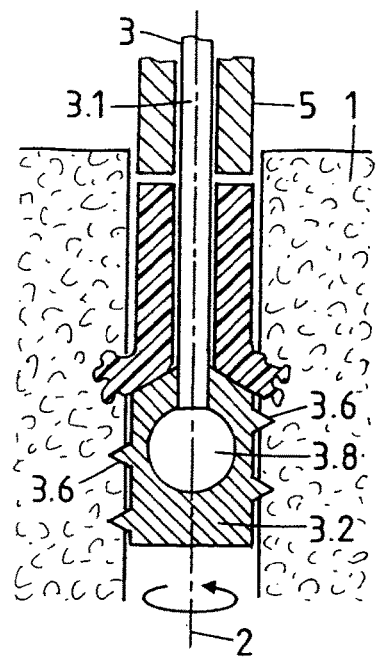
FIG. 6 shows yet another embodiment of a device and a method according to the invention.

When the implant comprises a threaded section or other mechanical fastening and/or retention structures, the rigidity of the augmentation material may cause the required force for insertion of the implant to be rather high. FIGS. 5 and 6 depict measures for reducing this force.

FIG. 5 depicts another embodiment of a device according to the invention. The lower panel shows a cross section through the device in the region of its distal end. The oscillation tool 3 depicted in FIG. 5 comprises several laterally protruding wing structures 3.7 (or blades). These wing structures prevent the augmentation material from flowing to certain angles and in addition may be sharpened so as to cut through already-hardened augmentation material as well as through bone tissue. Preferably, as in the depicted embodiment, the wing structures radially protrude into the bone tissue, and axially project further to the distal side than the periphery of the liquefaction interface, so as to sustainably prevent liquefied material from flowing to the angles to be kept free from augmentation material. The effect of the wing structures is to effectively slit the augmentation zone into different segments. By this, the augmented opening as a whole becomes more flexible for stretching, and a screw may be inserted more easily. Also, in weak or brittle bone tissue, when a torque is excerpted onto an augmentation zone 6 of the kind depicted in FIG. 6, there is a risk that the augmentation material including the trabeculae encased by it will break loose and rotate relative to the remaining bone tissue. This risk is effectively reduced by the splitting of the augmentation zone into unconnected segments.

A set-up as the one illustrated in FIG. 1, 2 or 5 may also be used if the energy coupled into the system is heat. In this case, the distal broadening 3.2 of the tool 3 may comprise a heating element.

If the energy is radiation energy, the roles of the tool and of the counter element are for example reversed, i.e. the counter element has a distal broadening distally of the augmentation element, and the tool, through which the radiation impinges onto the augmentation element, is proximal of the augmentation element. If the augmentation element is transparent for the used electromagnetic radiation, the radiation energy is for example coupled into the augmentation element and absorbed at the interface to the counter element. If the augmentation element is intransparent, the energy is absorbed at the interface to the tool.

The embodiment of FIG. 6 shows an oscillation tool of which the distal broadened portion 3.2 is formed by a rotation element that is mounted rotationally with respect to the shaft 3.1. To that end, the shaft comprises a distal enlargement 3.8 with which the rotation element 3.2 forms a swiveling positive-fit connection. Moreover, the distal broadening comprises thread cutting portions 3.6 radially protruding from the distal broadened portion 3.2. During the movement of the oscillation tool towards the proximal side, the distal broadened portion 3.2 rotates about the axis and thereby cuts an inner thread in the, for example, not yet fully hardened augmented zone 6. This, of course, also eases the insertion of an implant with an accordingly threaded section.

Figure 7:
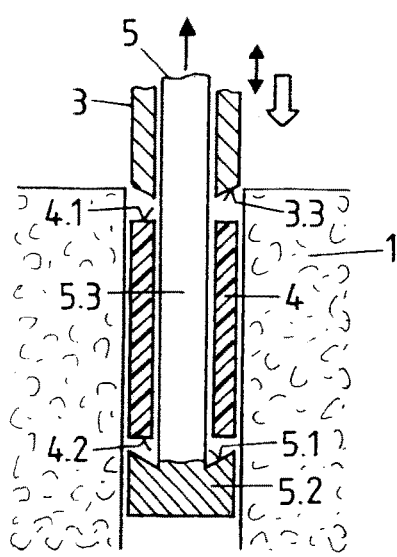
FIG. 7 shows an even further embodiment, with a forward movement of the oscillation tool.

The embodiment of FIG. 7 is an example of 'forward' insertion of the augmentation material: While in the above-described embodiments, a tensile force was coupled into the oscillation tool, and the liquefaction interface was at a distal end of the augmentation element 4, this is the other way round in the embodiment of FIG. 7. The oscillation tool 3 is a ring sonotrode acting on the augmentation element 4 on a proximal end surface 4.1 which thereby acts as the first augmentation element contact surface. The counter element 5 comprises a counter element shaft 5.3 reaching through the oscillation tool 3 and the augmentation element 4 to a distal end of the latter, where a distal broadening 5.2 of the counter element comprises a rearward (i.e. towards the proximal side) facing surface 5.1 that forms the counter element contact surface.

The oscillation tool contact surface 3.3 is preferably tapered outwardly. During the augmentation process, the oscillation thermoplastic material of the augmentation element is liquefied at the interface to the oscillation tool and is, by a pressure resulting form the force by which the oscillation tool and the counter element are pressed against each other, displaced towards the outside and into structures of the circumferential wall of the opening 1.1—similarly to the above-described embodiments. The counter element 5 during this process may be held still, or slowly pulled towards the proximal side. The augmentation process is continued until the oscillation tool contact surface 3.3 and the counter element contact surface 5.1 are in contact with each other or are at least close to each other so that the counter element can be removed to the proximal side.

Like for all other embodiments, the structures of the counter element 5 and of the (oscillation) tool 3 may optionally be adapted to each other so that when their contact surfaces meet at the end of the augmentation process, they match (i.e. the shapes correspond to each other so that they may rest against each other by way of a surface-to-surface contact), or that they at least rest against each other at the periphery so as to disrupt a connection between the augmentation material 6 and remaining thermoplastic material pulled out together with the oscillation tool 3 and the counter element 5.

While the embodiment of FIG. 7 features the disadvantage that there is a large surface contact between the oscillating oscillation tool 3 and the bone tissue as soon as the oscillation tool is inserted deeply into the opening 1.1, this embodiment may nevertheless be suitable for certain applications. For example, if a lot of augmentation material is to be brought into a volume directly underneath the surface (or underneath a comparably thin corticalis), the embodiment of FIG. 7 may be suitable. Especially, the whole propulsion then may come from the counter element while the oscillation tool remains immovable in its position protruding into the opening to a small extent only.

Figure 8:
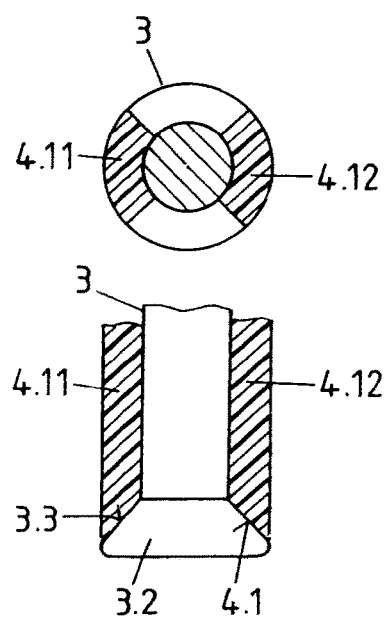
FIG. 8 illustrates the principle of a device where the augmentation element that is not all around, i.e. that does not cover the entire periphery.

In all above-described embodiments, the augmentation element 4 was assumed to be tube-shaped. While a generally tube shaped augmentation element is advantageous because such a shape is easy to guide during the augmentation process, is easy to handle and allows using easy-to-manufacture, symmetrical oscillation tools and counter elements, depending on the application also other shapes are feasible. FIG. 8 in the upper panel schematically illustrates a cross section through an oscillation-tool 3—augmentation element 4 assembly where the augmentation element is not circumferential but covers only certain angles. More concretely, it comprises two portions 4.11, 4.12 at lateral sides of the oscillation tool 3. The two portions may be discrete, or they may be connected, for example, by a connecting portion at the proximal end of the augmentation element 4. The lower panel of FIG. 8 illustrates a detail showing the liquefaction interface. In the depicted embodiment, the augmentation element 4.11, 4.12 is initially attached to the oscillation tool 3, so that the two portions are fixed to the tool and to each other prior to the augmentation process. Such attaching may, for example, be achieved by pressing the augmentation element portions against the oscillation tool contact surface 3.3 while either the augmentation element portions or the oscillation tool or both are at a temperature around the melting temperature, and thereafter letting the assembly cool. During the augmentation process, the augmentation element portions 4.11, 4.12 are held in place by the geometry of the oscillation tool and the opening in the tissue. In alternative embodiments, the augmentation element portions instead of being attached may also be inserted after the oscillation tool has been introduced.

As a remark, the attaching of the augmentation element to the oscillation tool and/or to the counter element prior to the augmentation process is an option in all embodiments of the invention. Such pre-assembly may be done during fabrication of the device, by the manufacturer, or immediately prior to the augmentation process by the user.

The counter element used for the oscillation-tool-augmentation-element-assembly of FIG. 8 may comprise distally protruding structures corresponding, in cross section and position, to the structure of the augmentation element portions and, after liquefaction, interdigitating with the oscillation tool so that the augmentation element material may be entirely liquefied and displaced when the oscillation tool and the counter element abut against each other.

A configuration as the one shown in FIG. 8 is suitable for augmenting hard tissue and/or hard tissue replacement material that with respect to the opening is not approximately cylindrical symmetric. An example of such a hard tissue and/or hard tissue replacement material would be a long bone where the opening's diameter approximately corresponds to the diameter of the trabecular portion, so that the augmentation material would have little room to go towards directions perpendicular to the bone axis. The bone axis would then be oriented parallel to the horizontal in the upper panel of FIG. 8. In addition or as an alternative, it is also suited for implementing the functionality of the device described with respect to FIG. 4, i.e. the division into a plurality of portions for different sectors (angle ranges) may also be effective to keep sectors of the augmentation material apart and to thereby ease the introduction of a screw or the like. The cutting wings (blades) may or may not be present when embodiment of FIG. 8 is used for such purpose.

Whereas in the above embodiments, the in hard tissue and/or hard tissue replacement material has been assumed to be trabecular bone tissue, the teaching equally well applies to other hard tissue and/or hard tissue replacement material. Also, in the described embodiments, the liquefaction interface was assumed to be the interface between the oscillation tool and the augmentation element, but the skilled person knowing the present teaching can readily transfer the teaching to configurations where liquefaction also or exclusively takes place at the interface to the counter element.

Example

In a configuration as described referring to FIG. 2, with circular symmetry with respect to the axis 2, the following device parameters were used: oscillation tool shaft diameter 2 mm, oscillation tool distal broadening diameter 4.4 mm, Taper inclination 45°. Tube shaped augmentation element inner diameter 2.1 mm, outer diameter 4.2 mm. Augmentation element material: LR708. Tube shaped counter element with approximately similar inner and outer diameters as the augmentation element (exact sizes of the diameters not critical). The oscillation tool and the counter element were metallic, for example of stainless steel (material not critical).

Insertion into an opening in sawbone 12.5 PCF with an opening diameter corresponding to or slightly above 4.4 mm. A Branson E150 apparatus was used for generating the mechanical oscillations coupled into the oscillation tool. The apparatus was operated at a frequency of 20 kHz and at a power of 105 W yielding good augmentation with a soundly anchored augmentation zone. Also tests with operating frequencies of 30 kHz were successful.

In a second example, a device with the above parameters but in addition with blades as illustrated in FIG. 5 were used, with otherwise the same operation parameters.

In the more general case, for any augmentation element dimensions, Sawbone 12.5 PCF is a suitable material for testing the suitability of the device. The required power approximately scales with the augmentation element cross section.

What is claimed is:

1. A device for preparing an opening in tissue for implantation of an implant, wherein the tissue is hard tissue, hard tissue replacement material or a combination of hard tissue and hard tissue replacement material, the device comprising:
   a tool adapted to be coupled to an energy source;
   a one-piece augmentation element of a thermoplastic material formed as a rotational symmetric tube; and,
   a counter element formed as a cylindrical rotationally symmetric tube,
   wherein the tool extends through both the augmentation element and the counter element, where a tool contact surface and a first augmentation element contact surface together form a first interface and where a second augmentation element contact surface and a counter element contact surface together form a second interface;
   wherein the device is configured to be inserted into an opening in the tissue;
   wherein the device is further configured for the augmentation element to be compressed between the tool and the counter element while at the same time energy is coupled into the tool;
   so that, when the device is inserted in the opening,
   (i) at least one of the first and the second interfaces serves as a liquefaction interface and forms part of a periphery of the device at least partially surrounded by a circumferential wall of the opening,
   (ii) material of the augmentation element in a vicinity of the liquefaction interface is liquefied when pressed against the tool contact surface by the effect of the energy coupled into the tool, to yield liquefied material, (iii) the liquefied material is displaced outwardly by compression of the augmentation element between the tool and the counter element, to yield liquefied displaced material, (iv) the liquefied displaced material is caused to penetrate into structures of the tissue; and, (v) compression of the augmentation element between the tool and the counter element causes the at least one liquefaction interface to move relative to the counter element or relative to the tool or relative to both, the counter element and the tool; and, wherein the augmentation element is configured to be liquefied by the energy to an extent that the tool and the counter element may be removed to a proximal side of the opening while the liquefied displaced material of the augmentation element remains in the structures to serve, after having hardened, as augmentation material.

2. The device according to claim 1, wherein the tool is an oscillation tool, being adapted to be coupled to an oscillation generator of mechanical oscillations as the energy source.

3. The device according to claim 1, wherein the tool contact surface is at a distal end of the augmentation element, and the force for compressing the augmentation element is couplable into the oscillation tool as tensile force.

4. The device according to claim 3, wherein the tool comprises a tool shaft and a tool distal broadening forming the tool contact surface.

5. The device according to claim 4, wherein the tool contact surface is tapered with respect to a normal the shaft such as to form a concave contact surface.

6. The device according to claim 4, wherein an outer diameter of the distal broadening is equal to or larger than an outer diameter of the augmentation element.

7. A kit of parts for anchoring an implant in hard tissue and/or hard tissue replacement material, the kit comprising: the device according claim 1 and further comprising an implant, wherein the implant is adapted to be implanted in the opening, and to thereby being anchored, at least in part, in the augmentation material.

8. The kit according to claim 7, wherein the implant comprises fastening structures or retention structures or fastening structures and retention structures for a mechanical anchoring in the augmentation material.

9. The kit according to claim 7, wherein the tool comprises a tool shaft and a tool broadening forming the tool contact surface, wherein an outer diameter of the implant is larger than an outer diameter of the tool broadening.

10. The kit according to claim 7, wherein the implant comprises thermoplastic surface portions weldable to the augmentation material.

* * * * *